United States Patent [19]

Meybeck et al.

[11] Patent Number: 5,603,949
[45] Date of Patent: * Feb. 18, 1997

[54] USE OF A TOCOPHEROL PHOSPHATE OR ONE OF ITS DERIVATIVES, FOR THE PREPARATION OF COSMETIC OR PHARMACEUTICAL COMPOSITIONS AND COMPOSITIONS SO OBTAINED

[75] Inventors: Alain Meybeck, Courbevoie; Marc Dumas, Colombes; Frédéric Bonte, Courbevoie; Christian Marechal, Paris, all of France

[73] Assignee: LVMH Recherche, Colombes Cedex, France

[ * ] Notice: The term of this patent shall not extend beyond the expiration date of Pat. No. 5,387,579.

[21] Appl. No.: 465,610

[22] Filed: Jun. 5, 1995

Related U.S. Application Data

[63] Continuation of Ser. No. 190,075, filed as PCT/FR92/00748, Jul. 30, 1992, abandoned.

[30] Foreign Application Priority Data

Aug. 1, 1991 [FR] France ..................... 91 09825

[51] Int. Cl.$^6$ ..................... A61K 9/127
[52] U.S. Cl. ............. 424/450; 428/402.2; 514/458; 549/220
[58] Field of Search .............. 424/450; 428/402.2; 514/458; 549/220

[56] References Cited

U.S. PATENT DOCUMENTS

| 4,617,292 | 10/1986 | Satoh | 514/27 |
| 4,914,197 | 4/1990 | Yamamoto | 536/117 |
| 5,114,957 | 5/1992 | Hendler | 514/356 |
| 5,387,579 | 2/1995 | Meybeck | 514/100 |

OTHER PUBLICATIONS

Suzuki Cosmetics & Toiletries 105, 1990.
Kubo. Chem. Pharm. Bull. 33 (6), 1985.
Halliwell. Free radicals in Biology & Medicine, 1991.

*Primary Examiner*—Gollamudi S. Kishore
*Attorney, Agent, or Firm*—Larson and Taylor

[57] ABSTRACT

Use of a tocopherol phosphate, other than alpha-tocopherol phosphate, especially in its dl or d form, or one of its esters having general formula (I) in which: R' is hydrogen atom, an alkyl radical having from 1 to 4 carbon atoms, such as the methyl or ethyl radical in particular, R'O is a tocopheryl radical; R" is a hydrogen atom, an alkyl radical having from 1 to 4 carbon atoms, such as the methyl or ethyl radical in particular, or R"O is an oxyethylene chain, of formula (a) in which $R_4$ and $R_5$ are independently a hydrogen atom or a methyl radical, and n is an integer of 1 or over; $R_1$, $R_2$ and $R_3$ are independently a hydrogen atom or a methyl radical, it being understood that $R_1$, $R_2$ and $R_3$ cannot simultaneously be a methyl radical. A represents the groups (b), or (c). The invention also concerns the use of cosmetically or of pharmaceutically acceptable salts of said compound in the preparation of a cosmetic or pharmaceutical, especially dermatological, composition characterized by having a reduced allergizing or irritating potential, or used in the prevention or treatment of allergic conditions, such as cutaneous allergy or bronchial or inflammatory asthma, or in the prevention or treatment of the harmful effects of free radicals.

34 Claims, No Drawings

USE OF A TOCOPHEROL PHOSPHATE OR ONE OF ITS DERIVATIVES, FOR THE PREPARATION OF COSMETIC OR PHARMACEUTICAL COMPOSITIONS AND COMPOSITIONS SO OBTAINED

This application is a continuation of application Ser. No. 08/190,075, filed as PCT/FR92/00748 Jul. 30, 1992, now abandoned.

The present invention relates in general terms to the use of a tocopherol phosphate or an ester or salt thereof for the preparation of cosmetic or pharmaceutical compositions, especially dermatological compositions, having an anti-allergic or anti-inflammatory activity or intended for the prevention or treatment of the harmful effects of free radicals, and to the cosmetic or pharmaceutical compositions, especially dermatological compositions, having an anti-allergic or anti-inflammatory activity or intended for the prevention or treatment of the harmful effects of free radicals, in which said compound is incorporated.

Vitamin E is known especially by the common name alpha-tocopherol (see Merck Index, 11th edition, reference 9832, page 1437).

alpha-Tocopherol is found in the natural state in a large number of plants, usually together with other compounds such as beta-tocopherol, gamma-tocopherol or delta-tocopherol.

It is also known that tocopherols occur in both the dl and d forms.

alpha-Tocopherol is essentially used for combating vitamin E deficiencies or as a nutritional factor, especially for combating muscular degeneration.

It is also used as an antioxidant, but at very specific doses.

α-Tocopherol esters, in particular the succinate, nicotinate or acetate, have also been described (Merck Index, 10th edition, references 9832, 9833, page 1437). The synthesis of alpha-tocopherol acetate is also described in the document U.S. Pat. No. 2,723,278 and the synthesis of other esters is described in the document J. Amer. Chem. Soc. (1943) 65, 918–924.

dl-alpha-Tocopherol phosphate is also known (see P. KARRER et al., Helv. Chim. Acta (1940) 23, 1137–8), as is its action on muscle metabolism (see J. Biol. Chem. 1942, 146, pages 309–321). Another document describes its biological role as an antioxidant on brain tissue (Biol. Antioxidants Trans., 1st Conf., 1946, pages 61–62). Its anticoagulant effect by acting on the polymerization of fibrin has also been described (Can. J. Biochem. and Physiol. 1959, 37, pages 501–505). Its in vitro antimicrobial action on B. subtilis and S. aureus has also been described (Naturwissenschaften 1960, 47, page 17).

It has now been discovered, totally surprisingly and unexpectedly, that tocopherol phosphates other than alpha-tocopherol phosphate, especially in their dl or d form, or of an ester or salt thereof possess an anti-allergic, anti-inflammatory and anti-free-radical activity, enabling them to be used advantageously for the preparation of cosmetic or pharmaceutical compositions, especially dermatological compositions, having a reduced allergizing or irritating potential or intended for the prevention or treatment of allergic or anti-inflammatory manifestations, or else for the prevention or treatment of the harmful effects of free radicals.

The object of the present invention is thus to solve the new technical problem which consists in the provision of an active substance having a good anti-allergic activity, especially for the prevention or treatment of skin allergy or bronchial asthma, or a good anti-inflammatory activity, or else a preventive or curative activity towards the harmful effects of free radicals, in particular by topical or general administration, thereby constituting a valuable active ingredient for the preparation of cosmetic or pharmaceutical compositions, especially dermatological compositions.

The present invention solves this new technical problem in a satisfactory manner by means of a particularly simple solution which can be used on the industrial scale.

Thus, according to a first feature, the present invention covers the use of a tocopherol phosphate other than alpha-tocopherol phosphate, especially in its dl or d form, or of an ester thereof, of general formula (I) below:

$$\text{(I)}$$

in which:

R' is a hydrogen atom or an alkyl radical having from 1 to 4 carbon atoms, such as the methyl or ethyl radical in particular, or R'O is a tocopheryl radical;

R" is a hydrogen atom or an alkyl radical having from 1 to 4 carbon atoms, such as the methyl or ethyl radical in particular, or R"O is an oxyethylenated chain of the formula $$-O-CH_2-\underset{\underset{R_4}{|}}{CH})_n-OR_5$$

in which $R_4$ and $R_5$ independently are a hydrogen atom or a methyl radical and n is an integer greater than or equal to 1;

$R_1$, $R_2$ and $R_3$ independently are a hydrogen atom or a methyl radical, it being understood that $R_1$, $R_2$ and $R_3$ cannot simultaneously be a methyl radical; and A is the group $$-CH_2-\underset{\underset{CH_3}{|}}{CH}- \quad \text{or} \quad -CH=\underset{\underset{CH_3}{|}}{C}-,$$

or of a cosmetically or pharmaceutically acceptable salt thereof, for the preparation of a cosmetic or pharmaceutical composition, especially dermatological composition, having a reduced allergizing or irritating potential or intended for the prevention or treatment of allergic manifestations such as skin allergy or bronchial asthma, or inflammatory manifestations, or for the prevention or treatment of the harmful effects of free radicals.

In the above formula, the preferred compounds are tocol, beta-tocopherol or 5,8-dimethyltocol, gamma-tocopherol or 7,8-dimethyltocol, zeta-2-tocopherol or 5,7-dimethyltocol, delta-tocopherol or 8-methyltocol, eta-tocopherol or 7-methyltocol, tocotrienol, zeta-1-tocopherol or 5,7,8-trimethyltocotrien-3',7',11'-ol, epsilon-tocopherol or 5,8-dimethyltocotrien-3',7',11'-ol, gamma-tocotrienol and delta-tocotrienol.

In one variant of the use according to the present invention, a mixture of tocopherol(s) phosphates, at least one of which is other than alpha-tocopherol phosphate, or of esters or salts thereof is used, said mixture being obtained especially by the phosphatization of a mixture of tocopherols extracted from a plant such as soya.

The tocopherol phosphates can be manufactured by the well-known process for the manufacture of alpha-tocopherol phosphate. A process for the preparation of alpha-tocopherol phosphate and salts thereof is described in the document JP-A-37-1737 in the name of Tomoda Pharm. Manuf. Co. Limited, to which those skilled in the art may refer.

The products used according to the present invention will thus be tocopherol phosphates other than alpha-tocopherol phosphate, or esters thereof, it being possible for these products to take the form of cosmetically or pharmaceutically acceptable salts, especially dermatological acceptable salts, such as, for example, alkali metal salts, especially sodium salts (monosodium or disodium salt), or alkaline earth metal salts, especially magnesium salts, or else ammonium salts or salts of primary, secondary or tertiary amines such as diethylamine, diethanolamine, triethylamine or triethanolamine in particular.

In formula (I), the alkyl radicals can have a linear or branched chain.

An alkyl radical having from 1 to 4 carbon atoms is for example methyl, ethyl, propyl, isopropyl or butyl, preferably methyl or ethyl.

Tocopheryl radical is understood as meaning the radical of formula (II) below:

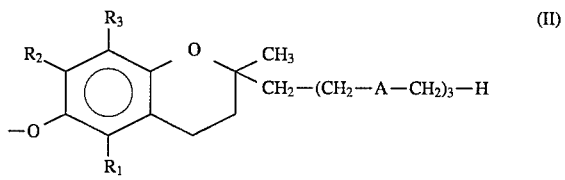

in which $R_1$, $R_2$ and $R_3$ independently are a hydrogen atom or a methyl radical and A is the group

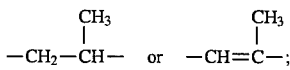

when R"O is an oxyethylenated chain, n will generally be greater than or equal to 1, for example between 2 and 50, preferably between 2 and 25 and in particular equal to 2 or 5.

In another advantageous embodiment according to the invention, a compound of formula I as defined above, preferably as a salt, is used in the form of small liposome-type vesicles obtained by the dispersion of said compound or said salt in water or an aqueous medium such as a buffer solution, especially by means of mechanical agitation followed by homogenization, for example by means of ultrasound or a homogenizer under pressure.

Preferably, the size of these vesicles is adjusted to a value of between about $6 \cdot 10^{-2}$ μm and 2 μm by modification of the homogenization parameters such as the energy and duration.

In one advantageous variant of the previous embodiment, the above-mentioned aqueous medium contains a biologically active agent, said agent being at least partially encapsulated, after dispersion, in the above-mentioned vesicles.

The above-mentioned active agent is preferably an anti-allergic substance such as an extract of Scutellaria, for example a root extract of Scutellaria baicalensis Georgi described in the document FR-A-2 628 317, or an anti-inflammatory substance.

In one advantageous embodiment of the use according to the invention, the concentration by weight of the above-mentioned compound of formula (I), of a salt thereof or of mixtures thereof is between 0.001 and 10%, preferably between 0.01% and 1% and particularly preferably between 0.05 and 0.5%, based on the total weight of the composition.

In a currently preferred embodiment, the above-mentioned compound of formula (I) is delta-tocopherol phosphate. The preferred salts are the monosodium salts and the disodium salt.

The compounds used according to the invention are generally available commercially and can be prepared especially by following procedures described in the literature, for example in Chem. Pharm. Bull. (1971), 19, (4), pages 687 to 695; Khim.-Pharm. Zh. (1983), 17, (7), pages 840 to 844; Khim.-Pharm. Zh. (1985), 19, (1), pages 75 to 77; or else in the patents U.S. Pat. No. 2,457,932 or JP-54-54 978.

The nomenclature of the tocopherols and compounds derived therefrom has been described in Europeénne J. Biochem. (1982), 123, 473–475. The preparation of delta-tocopherol has been described in J. Am. Chem. Soc. (1947), 69, pages 869–874. Likewise, the preparation of natural alpha-, beta- and gamma-tocopherol and those esters which are of physiological value has been described in J. Am. Chem. Soc. (1943), 65, pages 918–924. The document GB-A-900 085 describes yet another process for the manufacture of delta-tocopherol. The synthesis of zeta-1-tocopherol, epsilon-tocopherol and the tocotrienols is described in the document Helvetica Chimica Acta (1963), 46, pages 2517–2526. The synthesis of eta-tocopherol or 7-methyltocol is described in the document Nature (1956), 177, pages 86–87. Other information on the tocopherols can be found in the Merck Index, which is well known to those skilled in the art.

According to a second feature, the present invention covers a cosmetic or pharmaceutical composition, especially dermatological composition, having a reduced allergizing or irritating potential or intended especially for the prevention or treatment of allergic manifestations such as skin allergy or bronchial asthma, or inflammatory manifestations, or for the prevention or treatment of the harmful effects of free radicals, said composition comprising, as the active ingredient, at least one compound of formula (I) or a cosmetically or pharmaceutically acceptable salt thereof, as defined above.

In one variant, the compositions of the invention comprise, as the active ingredient, a mixture of tocopherol phosphates, at least one of which is other than alpha-tocopherol phosphate, or esters or salts thereof, obtained especially by the phosphatization of a mixture of tocopherols extracted from a plant such as soya.

In one advantageous embodiment, the cosmetic or dermatological composition comprises, as the active ingredient, at least one compound of formula (I) as defined above, preferably as a salt, in the form of small liposome-type vesicles obtained by the dispersion of said compound or said salt in water or an aqueous medium such as a buffer solution, especially by means of mechanical agitation followed by homogenization, for example by means of ultrasound or a homogenizer under pressure.

Preferably, the size of these vesicles is adjusted to a value of between about $6 \cdot 10^{-2}$ μm and 2 μm by modification of the homogenization parameters such as the energy and duration.

In one advantageous variant of the previous embodiment, the above-mentioned aqueous medium contains a biologically active agent, said agent being at least partially encapsulated, after dispersion, in the above-mentioned vesicles.

The above-mentioned active agent is preferably an anti-allergic substance such as an extract of Scutellaria, for example a root extract of Scutellaria baicalensis Georgi described in the document FR-A-2 628 317, or an anti-inflammatory substance.

In another advantageous embodiment, said cosmetic or dermatological compositions are prepared so as to have a reduced allergizing or irritating potential or so as to be intended for the prevention and treatment of allergic manifestations such as skin allergy or bronchial asthma, or inflammatory manifestations, or for the prevention or treatment of the harmful effects of free radicals.

The concentration of active ingredients in these cosmetic or dermatological compositions is as described above for the use.

The compositions according to the invention can be formulated in any form acceptable for their use in cosmetology, dermatology or pharmacy. In particular, they can be in the form of a cream for the prevention and cure of skin allergies, a soothing anti-allergic cream, a soothing anti-allergic oil, a preventive or curative anti-allergic lotion, an alcoholic after-shave lotion for soothing skin irritation, a hypoallergenic cream, a colloidal anti-asthmatic solution or else a solution intended for combating the toxic effects of the superoxide radicals which form during the application of resuscitation techniques with oxygen.

The compositions according to the invention can also be formulated as make-up compositions such as make-up foundation, lipstick, mascara or face powder.

According to a third feature, the present invention covers a process for reducing the allergizing or irritating potential of a pharmaceutical, dermatological or cosmetic composition, which consists in incorporating into said composition an effective amount of at least one compound of formula (I) or at least one salt thereof, as defined above.

In a currently preferred embodiment, the above-mentioned compound of formula (I) is beta-, gamma-, delta-, zeta-1- or zeta-2-, eta- or epsilon-tocopherol phosphate, gamma-tocotrienol, delta-tocotrienol or tocotrienol phosphate, or else tocol phosphate. The preferred salts are the monosodium salts and the disodium salt.

Advantageously, the concentration of compound of formula (I) or salt thereof is as described above for the use.

One variant of this process involves the incorporation of a mixture of tocopherol phosphates, at least one of which is other than alpha-tocopherol phosphate, or a salt or ester thereof, obtained especially by the phosphatization of a mixture of tocopherols extracted from a plant such as soya.

According to a fourth feature, the present invention further relates to a process for the manufacture of a cosmetic or dermatological composition having a reduced allergizing or irritating potential or intended in particular for the prevention or treatment of allergic manifestations such as skin allergy, or inflammatory manifestations, or for the prevention or treatment of the harmful effects of free radicals, said process comprising the incorporation of at least one compound of formula (I) or a salt thereof, as defined above, into a cosmetically or dermatologically acceptable excipient, vehicle or carrier.

According to a fifth feature, the present invention further relates to a process for the manufacture of a pharmaceutical composition having a reduced allergizing or irritating potential or intended for the prevention or treatment of allergic manifestations such as bronchial asthma, or inflammatory manifestations, or for the prevention or treatment of the harmful effects of free radicals, said process comprising the incorporation of at least one compound of formula (I) or a salt thereof, as defined above, into a pharmaceutically acceptable excipient, vehicle or carrier.

The incorporation of the compound of formula I or a salt thereof into said cosmetic, dermatological or pharmaceutical composition can be effected in different ways accessible to those skilled in the art, depending on the type of formula desired.

In one advantageous mode of carrying out said manufacturing processes, when the composition comprises an aqueous phase, the above-mentioned compound of formula (I) is first dispersed, preferably in the form of a salt as already defined, in water or said aqueous phase to form small vesicles, and the resulting dispersion is then mixed with any other constituents of the composition.

According to a sixth feature, the present invention covers a method of preventing or treating allergic manifestations such as skin allergy or bronchial asthma, or inflammatory manifestations, or preventing or treating the harmful effects of free radicals, said method comprising the general or topical administration, to the regions of the body to be treated, of an effective amount of at least one compound of formula (I) or a salt thereof, as defined above, incorporated in a cosmetically, dermatologically or pharmaceutically acceptable excipient, vehicle or carrier.

According to a seventh feature, the present invention further covers, by way of novel products, tocol, tocotrienol, epsilon-tocopherol, zeta-1- or zeta-2-tocopherol or eta-tocopherol monophosphate or diphosphate and beta-, gamma- or delta-tocopherol diphosphate, as well as salts and esters thereof.

The invention will now be illustrated in detail with the aid of several Examples, which are given simply by way of illustration and cannot in any way limit the scope of the invention.

The percentages are given by weight in the Examples, unless indicated otherwise.

EXAMPLE 1 a) Preparation of the disodium salt of delta-tocopherol phosphate

The reaction scheme is as follows:

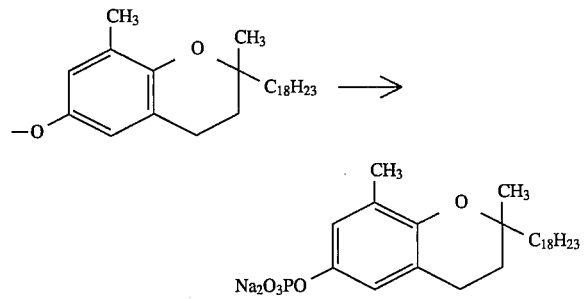

1) $POCl_3$, $Et_3N$, $-20°$ C., 4 h. 2) $H_2O$, reflux, 3 h.
3) NaOH/MeOH 8.53 g (55.7 mmol) of phosphorus oxychloride in 80 ml of previously distilled isopropyl ether are placed in a 500 ml round-bottomed flask equipped with a magnetic stirrer, a thermometer, a dropping funnel and an argon balloon. A solution of 20 g (49.6 mmol) of delta-tocopherol and 9.04 g (89.3 mmol) of triethylamine in 200 ml of isopropyl ether is then added at $-20°$ C. (the addition takes about 2 h). Stirring is continued for 2 h at $-20°$ C. and 20 ml of water are then added, the mixture being allowed to warm up to room temperature. It is subsequently refluxed for 3 h and then cooled. The aqueous phase is drawn off, the reaction medium is evaporated to one-third of its volume and 50 ml of a 10% methanolic solution of sodium hydroxide are added, with stirring. The solvent is evaporated off and the yellowish paste obtained is washed with 20 ml of methanol cooled to $-20°$ C. The paste is then dried with a vane pump at 60° for 12 h to give 20.3 g (78%) of the disodium salt of delta-tocopherol.

Characteristics of the resulting sample:

$^{31}P$ NMR ($CDCl_3$)

5.9 ppm (monophosphate), −10.67 ppm (pyrophosphate)

Sodium content % Na calculated 8.73% found 5.86% b) Preparation of a solution of the disodium salt of delta-tocopherol phosphate 0.8 g of the powdered disodium salt of delta-tocopherol phosphate obtained according to step a) above is weighed out.

This powder is poured into 96.2 g of double-distilled water, with stirring, and stirring is continued for about 2 hours.

This gives a solution of the disodium salt of delta-tocopherol phosphate.

c) Preparation of a suspension of delta-tocopherol acid phosphate

The pH of the solution obtained in step b) is lowered to 7 by the addition of about 3 ml of 0.5N HCl, with stirring, and the pH is then adjusted to 6.0 with 0.1N HCl, with stirring. The tocopherol phosphate is then in the acid form at this pH.

Homogenization is then carried out by means of ultrasound for 10 min at 150 W until a clear suspension is obtained, thereby producing liposome-type vesicles of tocopherol acid phosphate.

In the case of larger volumes, it can be advantageous to use a homogenizer under pressure, for example a homogenizer of the Manton-Gaulin® type at a pressure of about 500 bar.

The size of the vesicles of delta-tocopherol acid phosphate obtained in this way can be determined for example by means of an Autosizer 2C from MALVERN. In this Example, the measured mean size is of the order of 130 nm.

It will also be noted that various dilutions can be prepared by modification of the amount of compounds initially added or by modification of the volume of the dispersion solution, which constitutes an easy process for the preparation of various concentrations of active principle.

In the Example described, about 100 g of suspension were obtained which contained about 0.8% of delta-tocopherol acid phosphate in the form of liposome-type vesicles of substantially homogeneous sizes.

d) Preparation of a gelled composition of delta-tocopherol phosphate

The homogenized suspension obtained above in step c) can be gelled by mixing with a gel such as a vinylic polymer gel, in particular that marketed under the tradename Carbopol® 940.

In a manner known per se, this gel can be prepared for example by dispersing 1 g of Carbopol® 940 in 99 g of water in the presence of a preservative, and then, after swelling, by neutralizing the dispersion to pH 7.5, for example with triethanolamine.

100 g of this gel are added to the 100 g of homogenized suspension obtained above. This gives a gelled composition in which the concentration of delta-tocopherol phosphate is about 0.4%.

Gelled compositions containing various concentrations of delta-tocopherol phosphate can be obtained by following the procedure indicated above.

EXAMPLE 2

Demonstration of the inhibition of phospholipase $A_2$ (or $PLA_2$)

The inhibition of phospholipase $A_2$, which is involved in the production of allergy and inflammation mediators, especially in the inflammatory reaction of skin allergies, is measured according to the protocol described by H. W. Chang, I. Kudo, M. Tomita and K. Inoue in J. Biochem. (Tokyo) 102(1): 147–154 (1987).

The phospholipase $A_2$ is isolated from the peritoneal cavity of a rat. $PLA_2$ hydrolyzes the ester linkage in the 2-position of the glycerol of a phosphatidylethanolamine, this position being occupied by a fatty acid residue labeled with carbon 14. The radioactive fatty acid released will be extracted and then quantitatively analyzed by liquid scintillation. In the presence of the $PLA_2$ inhibitor, this hydrolysis will be reduced and less released fatty acid will therefore be determined.

In practice, the $PLA_2$ and the test product are placed in a 0.1M Tris-HCl buffer, pH=9, containing 4 mmol of $Ca^{++}$ and the mixture is incubated for 20 min at 37° C., with agitation. After this contact time, the labeled phosphatidylethanolamine is added and incubation is continued for 20 min at 37° C., with agitation, to allow the hydrolysis of this substrate. n-Heptane is then used to extract the labeled fatty acid released during the hydrolysis, the latter then being quantitatively analyzed by liquid scintillation. The 50% inhibitory concentration ($IC_{50}$), i.e. the concentration of test product at which the amount of labeled fatty acid released is half that obtained in the absence of product (control), is then determined.

Thus an $IC_{50}$ of 10 μg/ml is obtained with the disodium salt of delta-tocopherol phosphate prepared in step b) of Example 1. This concentration is low and shows that the disodium salt of delta-tocopherol phosphate has a very good inhibitory activity.

Examples of pharmaceutical or cosmetic formulations containing vitamin E phosphate

EXAMPLE 3

Cream for the prevention and cure of skin allergies

| Composition: | | |
|---|---|---|
| A | Cera bellina | 5.00 g |
|   | Silicone 200 | 1.50 g |
|   | Squalane | 5.00 g |
|   | Myglyol 812 | 5.00 g |
|   | Nylon 12 SP 500 | 3.00 g |
|   | BHT | 0.05 g |
| B | Demineralized water | 49.56 g |
|   | EDTA | 0.10 g |
|   | Propylene glycol | 4.00 g |
|   | Carbopol ® 1342 | 0.45 g |
|   | Triethanolamine | 0.54 g |
|   | 0.4% dispersion of delta-tocopherol phosphate, pH 6.6 | 25.00 g |
| C | Germaben II ® | 0.80 g |

Procedure: Mixture A is heated, with stirring, to give a homogeneous mixture. To prepare mixture B, the Carbopol® 1342 is dispersed in an aqueous solution containing the EDTA and the propylene glycol in 49.56 g of distilled water and the dispersion is neutralized with the triethanolamine. The 0.4% dispersion (non-gelled) of delta-tocopherol phosphate obtained according to Example 1 is then added.

Mixture B is then heated to 75° C. and kept at this temperature, with stirring, while mixture A is added. The resulting mixture is allowed to cool to 45° C., the Germaben II® is then added and the mixture is allowed to cool further to room temperature, with stirring.

This gives a cream.

EXAMPLE 4

Soothing anti-allergic cream

| Composition: | | |
|---|---|---|
| A | Soya lecithin | 2.00 g |
|   | Vegetable oil | 8.50 g |
| B | Demineralized water | 58.85 g |
|   | EDTA | 0.10 g |
|   | Glycerol | 4.00 g |
|   | Carbopol® 940 | 0.35 g |
|   | Triethanolamine | 0.40 g |
|   | Germaben II® | 0.80 g |
| C | 0.4% dispersion of delta-tocopherol phosphate, pH 6.6 | 25.00 g |

Procedure: The vegetable oil and the lecithin are heated, with stirring, until a complete solution has formed, and this solution is allowed to cool to room temperature. Mixture B is obtained by dispersing the Carbopol® 940 in a water+EDTA+glycerol mixture. The whole is neutralized with the triethanolamine, after which the Germaben II® is added.

Mixture A is then poured into mixture B, with stirring. The resulting mixture is homogenized and the dispersion obtained as in Example 1 is then added. Further homogenization gives a cream which can be used morning and evening by local application to soothe allergic skin reactions.

EXAMPLE 5

Soothing anti-allergic oil 0.1 g of powdered disodium gamma-tocopherol phosphate, prepared by a procedure similar to that of Example 1, is dissolved in 99.9 g of trioctyl citrate at 70° C. for 8 h, with magnetic stirring.

The resulting oily solution can be used by local application in the same way as the cream of Example 4.

EXAMPLE 6

Alcoholic after-shave lotion

| Composition: | |
|---|---|
| Disodium tocol phosphate | 0.2 g |
| Ethanol | 40 g |
| Propylene glycol | 0.5 g |
| Pantothenol | 0.1 g |
| Perfumed aqueous excipient qsp | 100 g |

Preparation: The disodium tocol phosphate, prepared by a procedure similar to that of Example 1, is dissolved in the absolute alcohol, and the other constituents are dissolved in the water in a separate operation. The two solutions obtained are mixed and the whole is homogenized by means of ultrasound.

This lotion can be used to soothe the irritation due to shaving, which is commonly known as "smarting".

EXAMPLE 7

Preventive or curative anti-allergic lotion

| Composition: | |
|---|---|
| Dispersion of the phosphate of a mixture of tocopherols extracted from soya, containing 4% of tocopherol phosphate | 25.00 g |
| Ethanol | 10.00 g |
| Propylene glycol | 5.00 g |
| Aqueous excipient qsp | 100.00 g |

The 4% dispersion of the phosphate of tocopherols extracted from soya is prepared as in Example 1b), except that it has a higher concentration of tocopherol phosphate.

The constituents of the above formulation are mixed together and homogenized by means of ultrasound.

EXAMPLE 8

Colloidal anti-asthmatic solution

| Composition: | |
|---|---|
| 4% dispersion of zeta-2-tocopherol phosphate | 12.50 g |
| Buffered aqueous excipient + preservative qsp | 100.00 g |

The dispersion of monosodium zeta-2-tocopherol phosphate is prepared as in Example 1. After homogenization by means of ultrasound, a colloidal solution is obtained which is then incorporated into the buffered excipient.

This solution can be used by spraying into the upper respiratory tract, especially for soothing asthmatic coughs.

EXAMPLE 9

Colloidal solution for resuscitation techniques

| Composition: | |
|---|---|
| 4% dispersion of epsilon-tocopherol phosphate | 7.50 g |
| Buffered aqueous excipient + preservative qsp | 100.00 g |

This composition is prepared as in the previous Example.

It can be used for combating the toxic effects of the superoxide radicals which form during the application of resuscitation techniques with oxygen. In this case it is administered by intratracheal instillation at the same time as the gaseous mixture is administered.

EXAMPLE 10

Anti-allergic make-up foundation

| Composition: | |
|---|---|
| Disodium gamma-tocopherol phosphate | 0.5 g |
| Pigmented emulsion for make-up foundation | 99.5 g |

This composition is prepared by incorporating the disodium tocopherol phosphate, previously dispersed in water, into the aqueous phase of the emulsion. The pigmented emulsion is then produced by the conventional procedure.

This make-up foundation minimizes the risks of allergic manifestations due to a raw material or to an allergenic substance coming into contact with the skin.

What is claimed is:

1. A cosmetic or pharmaceutical composition consisting essentially of (I) 0.001 to 10% concentration by weight of a tocopherol phosphate selected from the group consisting of:

(a) a tocopherol phosphate of general formula:

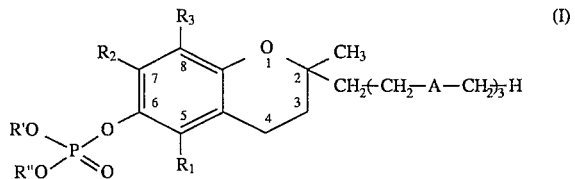

in which:

R' is selected from the group consisting of a hydrogen atom, an alkyl radical having 1 to 4 carbon atoms and a tocopherol radical when R' is in the form of R'O;

R" is selected from the group consisting of a hydrogen atom, an alkyl radical having 1 to 4 carbon atoms and, when R" is in the form of R"O, an oxyethylenated chain of the formula:

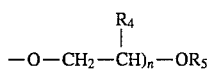

in which $R_4$ and $R_5$ independently are selected from the group consisting of a hydrogen atom and a methyl radical, and n is an integer greater than or equal to 1;

$R_1$, $R_2$ and $R_3$ independently are selected from the group consisting of a hydrogen atom and a methyl radical, with the proviso that $R_1$, $R_2$ and $R_3$ cannot simultaneously be a methyl radical; and A is the group:

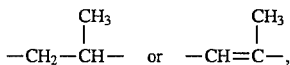

(b) zeta-1-tocopherol phosphate;
   (c) an ester of the tocopherol phosphate of part (a);
   (d) an ester of the zeta-1-tocopherol phosphate of part (b);
   (e) a cosmetically or pharmaceutically acceptable salt of the tocopherol phosphate of part (a); and
   (f) a cosmetically or pharmaceutically acceptable salt of the zeta-1-tocopherol phosphate of part (b);

and (II) a cosmetically, dermatologically or pharmaceutically acceptable excipient, vehicle or carrier.

2. A composition according to claim 1, wherein the tocopherol phosphate is selected from the group consisting of tocol, 5,8-dimethyltocol, 7,8-dimethyltocol, 5,7-dimethyltocol, 8-methyltocol, 7-methyltocol, tocotrienol, 5,7,8-trimethyltocotrien-3',7',11'-ol, 5 8-dimethyltocotrien-3',7',11'-ol, gamma-tocotrienol and delta-tocotrienol.

3. A composition according to claim 1 wherein the tocopherol phosphate is obtained by the phosphatization of a mixture of non-alpha tocopherols extracted from a tocopherol phosphate-containing plant.

4. A composition according to claim 1 wherein the tocopherol phosphate is in the form of liposome vesicles obtained by the dispersion of said tocopherol phosphate in water or an aqueous medium.

5. A composition according to claim 4 wherein the antiallergic substance is an extract of Scutellaria.

6. A composition according to claim 5 wherein the extract is a root extract of Scutellaria baicalensis Georgi.

7. A composition according to claim 4 wherein the size of the vesicles is between about $6 \cdot 10^{-2}$ μm and 2 μm.

8. A composition according to claim 1 wherein the concentration by weight of the tocopherol phosphate is between 0.01% and 1% of the total weight of the composition.

9. A composition according to claim 1 wherein the concentration by weight of the tocopherol phosphate is between 0.05% and 0.5% of the total weight of the composition.

10. A composition according to claim 1 wherein the salt of the tocopherol phosphate of part (a) or the zeta-1-phosphate of part (b) is selected from the group consisting of a monosodium salt and a disodium salt.

11. A process for the treatment of skin allergy or bronchial asthma comprising administering to a patient, in an amount effective to treat skin allergy or bronchial asthma, at least one cosmetic or pharmaceutical composition consisting essentially of (I) 0.001 to 10% concentration by weight of a tocopherol phosphate selected from the group consisting of:

(a) a tocopherol phosphate of general formula:

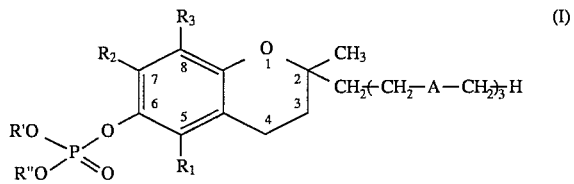

in which:

R' is selected from the group consisting of a hydrogen atom, an alkyl radical having 1 to 4 carbon atoms and a tocopherol radical when R' is in the form of R'O;

R" is selected from the group consisting of a hydrogen atom, an alkyl radical having 1 to 4 carbon atoms and, when R" is in the form of R"O, an oxyethylenated chain of the formula:

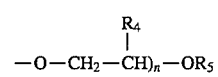

in which $R_4$ and $R_5$ independently are selected from the group consisting of a hydrogen atom and a methyl radical, and n is an integer greater than or equal to 1;

$R_1$, $R_2$ and $R_3$ independently are selected from the group consisting of a hydrogen atom and a methyl radical, with the proviso that $R_1$, $R_2$ and $R_3$ cannot simultaneously be a methyl radical; and A is the group:

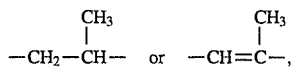

(b) zeta-1-tocopherol phosphate;
    (c) an ester of the tocopherol phosphate of part (a);
    (d) an ester of the zeta-1-tocopherol phosphate of part (b);
    (e) a cosmetically or pharmaceutically acceptable salt of the tocopherol phosphate of part (a); and
    (f) a cosmetically or pharmaceutically acceptable salt of the zeta-1-tocopherol phosphate of part (b);

and (II) a cosmetically, dermatologically or pharmaceutically acceptable excipient, vehicle or carrier.

12. A process according to claim 11 wherein the tocopherol phosphate is selected from the group consisting of tocol, 5,8-dimethyltocol, 7,8-dimethyltocol, 5,7-dimethyltocol, 8-methyltocol, 7-methyltocol, tocotrienol, 5,7,8-trimethyltocotrien-3',7',11'-ol, 5 8-dimethyltocotrien-3',7',11'-ol, gamma-tocotrienol and delta-tocotrienol.

13. A process according to claim 11 wherein the salt of the tocopherol phosphate of part (a) or the zeta-1-phosphate of part (b) is selected from the group consisting of a monosodium salt and a disodium salt.

14. A process according to claim 13 wherein the concentration by weight of the tocopherol phosphate is between 0.001% and 10% based on the total weight of the composition.

15. The process of claim 13 wherein said concentration by weight of the tocopherol phosphate is between 0.01% and 1% based on the total weight of the composition.

16. The process of claim 13 wherein said concentration by weight of the tocopherol phosphate is between 0.05% and 0.5% based on the total weight of the composition.

17. The process of claim 13 wherein the tocopherol phosphate comprises a mixture obtained by the phosphatization of a mixture of tocopherols extracted from a tocopherol phosphate-containing plant.

18. The process of claim 17 wherein said plant is a soya plant.

19. The process of claim 13 wherein the tocopherol phosphate is in the form of liposome vesicles obtained by the dispersion of said tocopherol phosphate in water or an aqueous medium.

20. The process of claim 19 wherein the aqueous medium contains a biologically active agent, and wherein said process further comprising the step of at least partially encapsulating said biologically active agent in the vesicles.

21. The process of claim 20 wherein the biologically active agent is selected from the group consisting of an anti-allergic substance and an anti-inflammatory substance.

22. The process of claim 21 wherein the anti-allergic substance is an extract of Scutellaria.

23. The process of claim 22 wherein the extract is a root extract of Scutellaria baicalensis Georgi.

24. The process of claim 19 wherein the size of the vesicles is between about $6 \cdot 10^{-2}$ µm and 2 µm.

25. A composition according to claim 1 wherein said composition is in the form of a cream for the treatment of skin allergies.

26. A composition according to claim 1 wherein said composition is in the form of a soothing anti-allergic cream.

27. A composition according to claim 1 wherein said composition is in the form of a soothing anti-allergic oil.

28. A composition according to claim 1 wherein said composition is in the form of a anti-allergic lotion.

29. A composition according to claim 1 wherein said composition is in the form of an alcoholic after-shave lotion for soothing skin irritation.

30. A composition according to claim 1 wherein said composition is in the form of a hypoallergenic cream.

31. A composition according to claim 1 wherein said composition is in the form of a colloidal anti-asthmatic solution.

32. A cosmetic or pharmaceutical composition consisting essentially of (I) 0.001 to 10% concentration by weight of a tocopherol phosphate selected from the group consisting of:

(a) a tocopherol phosphate of general formula:

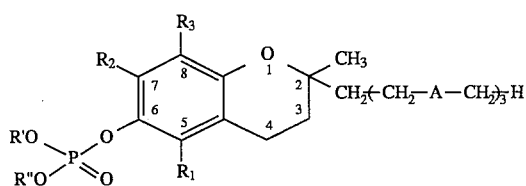

(I)

in which:

R' is selected from the group consisting of a hydrogen atom, an alkyl radical having 1 to 4 carbon atoms and a tocopherol radical when R' is in the form of R'O;

R" is selected from the group consisting of a hydrogen atom, an alkyl radical having 1 to 4 carbon atoms and, when R" is in the form of R"O, an oxyethylenated chain of the formula:

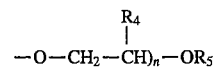

in which $R_4$ and $R_5$ independently are selected from the group consisting of a hydrogen atom and a methyl radical, and n is an integer greater than or equal to 1;

$R_1$, $R_2$ and $R_3$ independently are selected from the group consisting of a hydrogen atom and a methyl radical, with the proviso that $R_1$, $R_2$ and $R_3$ cannot simultaneously be a methyl radical; and A is the group:

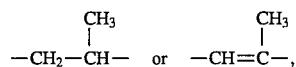

(b) zeta-1-tocopherol phosphate;

(c) an ester of the tocopherol phosphate of part (a);

(d) an ester of the zeta-1-tocopherol phosphate of part (b);

(e) a cosmetically or pharmaceutically acceptable salt of the tocopherol phosphate of part (a); and (f) a cosmetically or pharmaceutically acceptable salt of the zeta-1-tocopherol phosphate of part (b);

(II) a biologically active agent selected from the group consisting of an anti-allergic substance and an anti-inflammatory substance;

and (III) a cosmetically, dermatologically or pharmaceutically acceptable excipient, vehicle or carrier.

33. A composition according to claim 1 wherein the tocopherol phosphate is selected from the group consisting of a dl form of the tocopherol phosphate of part (a) and the d form of the tocopherol phosphate of part (a), and wherein the zeta-1-phosphate is selected from the group consisting of a dl form of the zeta-1-tocopherol phosphate of part (b) and a d form of the zeta-1-tocopherol phosphate of part (b).

34. A process according to claim 11 wherein the tocopherol phosphate of the cosmetic or pharmaceutical composition is selected from the group consisting of a dl form of the tocopherol phosphate of part (a) and the d form of the tocopherol phosphate of part (a), and wherein the zeta-1-phosphate is selected from the group consisting of a dl form of the zeta-1-tocopherol phosphate of part (b) and a d form of the zeta-1-tocopherol phosphate of part (b).

* * * * *